United States Patent [19]
Karrer

[11] Patent Number: 5,192,803
[45] Date of Patent: Mar. 9, 1993

[54] SULFENYLATED CARBAMIC ESTERS AND THEIR USE IN PESTICIDES

[75] Inventor: Friedrich Karrer, Zofingen, Switzerland

[73] Assignee: Ciba-Geigy Corporation, Ardsley, N.Y.

[21] Appl. No.: 719,870

[22] Filed: Jun. 24, 1991

Related U.S. Application Data

[63] Continuation-in-part of Ser. No. 508,149, Apr. 11, 1990, abandoned.

[30] Foreign Application Priority Data

Apr. 14, 1989 [CH] Switzerland ............... 1422/89

[51] Int. Cl.$^5$ ............ A61K 31/325; C07C 309/32; C07C 321/16; C07C 381/14
[52] U.S. Cl. ................ 514/539; 560/12; 560/16; 560/17; 562/430; 562/431
[58] Field of Search ............. 560/12, 16, 17; 562/430, 431; 514/539

[56]  References Cited
U.S. PATENT DOCUMENTS

| | | | |
|---|---|---|---|
| 4,080,470 | 3/1978 | Karrer | 424/300 |
| 4,215,139 | 7/1980 | Fischer et al. | 424/300 |
| 4,413,010 | 11/1983 | Zurfluh | 424/300 |
| 4,555,405 | 11/1985 | Boger et al. | 514/488 |
| 4,608,389 | 8/1986 | Kisida et al. | 514/539 |
| 4,745,128 | 5/1988 | Vjvari et al. | 514/483 |

FOREIGN PATENT DOCUMENTS 3320534 12/1983 Fed. Rep. of Germany.
3334983 4/1984 Fed. Rep. of Germany.

Primary Examiner—Jose G. Dees
Assistant Examiner—Vera C. Clarke
Attorney, Agent, or Firm—Kevin T. Mansfield; Edward McC. Roberts

[57] ABSTRACT

Novel substituted 2-phenoxyphenoxyethylcarbamic esters of the formula I

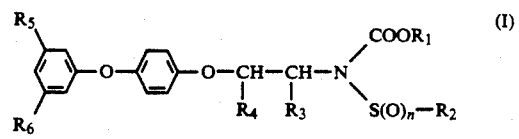

where $R_1$ is $C_1$-$C_4$alkyl or $C_3$-$C_4$alkenyl, $R_2$ is $C_1$-$C_4$alkyl or a radical of the formula

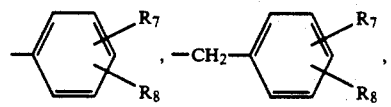

—$C(CH_3)_2$—CN or —$N(R_9)$—COO—$C_1$-$C_4$alkyl, $R_3$ and $R_4$ independently of one another are hydrogen or methyl, $R_5$ is fluorine or chlorine, $R_6$ is either identical to the substituents given in the case of $R_5$ or is hydrogen, $R_7$ and $R_8$ independently of one another are hydrogen, halogen, $C_1$-$C_4$alkyl, $C_1$-$C_4$alkoxy or nitro, $R_9$ is $C_1$-$C_4$alkyl and n is zero, one or two, their preparation, their use in pest control, and pesticides containing these carbamic esters as active substance, are described. The preferred field of application is the control of pests on animals and plants, in partcular of eggs and larvae of phytophagous harmful insects and harmful mites.

10 Claims, No Drawings

SULFENYLATED CARBAMIC ESTERS AND THEIR USE IN PESTICIDES

CROSS REFERENCE TO RELATED APPLICATIONS

This is a continuation-in-part of application Ser. No. 508,149 filed on Apr. 11, 1990 abandoned.

The present invention relates to novel substituted 2-phenoxyphenoxyethylcarbamic esters, to their preparation, to their use in pest control, and to pesticides containing these carbamic esters as active substance.

The carbamic esters according to the invention are those of the formula I

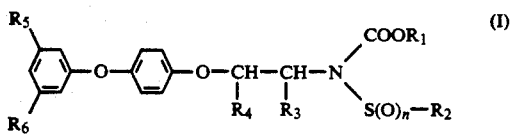

where $R_1$ is $C_1$-$C_4$alkyl or $C_3$-$C_4$alkenyl, $R_2$ is $C_1$-$C_4$alkyl or a radical of the formula

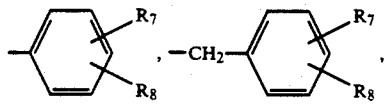

—$C(CH_3)_2$—CN or —$N(R_9)$—COO—$C_1$-$C_4$alkyl, $R_3$ and $R_4$ independently of one another are hydrogen or methyl, $R_5$ is fluorine or chlorine, $R_6$ is either identical to the substituents given in the case of $R_5$ or is hydrogen, $R_7$ and $R_8$ independently of one another are hydrogen, halogen, $C_1$-$C_4$alkyl, $C_1$-$C_4$alkoxy or nitro, $R_9$ is $C_1$-$C_4$alkyl and n is zero, one or two.

Halogen in the definition of $R_7$ and $R_8$ is to be understood as meaning fluorine, chlorine, bromine or iodine, but preferably chlorine.

$C_1$-$C_4$Alkyl groups can be straight-chain or branched. Examples of such radicals which may be mentioned are methyl, ethyl, propyl, isopropyl or butyl and its isomers. The preferred alkyl group is ethyl. $C_1$-$C_4$Alkenyl groups have the double bond preferably in the 2-position, as is the case in allyl, methallyl or 2-butenyl. The preferred alkenyl group is allyl.

Within the scope of the present invention, $C_1$-$C_4$alkoxy radicals of the definition of $R_7$ and $R_8$ are methoxy, ethoxy, propoxy, isopropoxy or the four butoxy isomers. Methoxy is preferred.

If the radical $R_6$ has a meaning other than hydrogen, i.e. if it is fluorine or chlorine, then the meaning within the scope of this invention is that $R_6$ is the same halogen atom as $R_5$.

Pesticidal ethyl carbamic acid derivatives have already been disclosed in various publications, but these substances are not satisfactory with regard to the spectrum of action obtained, or only in some cases. Examples of such compounds are disclosed in U.S. Pat. Nos. 4,080,470, 4,215,139, 4,413,010, 4,555,405, 4,608,389 and 4,745,128 and the German Offenlegungsschriften DE-OS 3,320,534, 3,334,983 and 3,706,082. There is therefore still a demand for active substances of this substance class which have improved properties.

It has now been found that the compounds of the formula I according to the invention are valuable active substances in pest control while the tolerance by homothermals, fish and plants is favourable. The use of the active substances according to the invention relates to arthropods in particular insects and arachnids which are encountered in crop plants and ornamental plants in agriculture, in particular in plantations of cotton, vegetables and fruit, in forests, in the protection of stored goods and materials, and in the hygiene field, in particular on domestic animals and livestock. They are active against all or individual development stages of normally-sensitive but also resistant species. Their action can be demonstrated by an immediate, or somewhat delayed, destruction of the pests, for example during ecdysis or by a lower number of eggs deposited and/or a lower hatching rate. The abovementioned pests include:

from the order of the Lepidoptera, for example Acleris spp., Adoxophyes spp., Aegeria spp., Agrotis spp., *Alabama argillaceae*, Amylois spp., *Anticarsia gemmatalis*, Archips spp., Argyrotaenia spp., Autographa spp., *Busseola fusca, Cadra cautella, Carposina nipponensis*, Chilo spp., Choristoneura spp., *Clysia ambiguella*, Cnaphalocrocis spp., Cnephasia spp., Cochylis spp., Coleophora spp., *Crocidolomia binotalis, Cryptophlebia leucotreta*, Cydia spp., Diatraea spp., *Diparopsis castanea*, Earias spp., Ephestia spp., Eucosma spp., *Eupoecilia ambiguella*, Euproctis spp., Euxoa spp, Grapholita spp., *Hedya nubiferana*, Heliothis spp., *Hellula undalis, Hyphantria cunea, Keiferia lycopersicella Leucoptera scitella*, Lithocollethis spp., *Lobesia botrana*, Lymantria spp., Lyonetia spp., Malacosoma spp., *Mamestra brassicae, Manduca sexta*, Operophtera spp., *Ostrinia nubilalis*, Pammene spp., Pandemis spp., *Panolis flammea, Pectinophora gossypiella, Phthorimaea operculella, Pieris rapae*, Pieris spp., *Plutella xylostella*, Prays spp., Scirpophaga spp., Sesamia spp., Sparganothis spp., Spodoptera spp., Synanthedon spp., Thaumetopoea spp., Tortrix spp., *Trichoplusia ni* and Yponomeuta spp.;

from the order of the Coleoptera, for example Agriotes spp., Anthonomus spp., *Atomaria linearis, Chaetocnema tibialis*, Cosmopolites spp., Curculio spp., Dermestes spp., Diabrotica spp., Epilachna spp., Eremnus spp., *Leptinotarsa decemlineata*, Lissorhoptrus spp. Melolontha spp., Orycaephilus spp., Otiorhynchus spp., Phlyctinus spp., Popillia spp., Psylliodes spp., Rhizopertha spp., Scarabeidae, Sitophilus spp., Sitotroga spp., Tenebrio spp., Tribolium spp. and Trogoderma spp.;

from the order of the Orthoptera, for example Blatta spp., Blattella spp., Gryllotalpa spp., *Leucophaea maderae*, Locusta spp., Periplaneta spp. and Schistocerca spp.;

from the order of the Isoptera, for example Reticulitermes spp.;

from the order of the Psocoptera, for example Liposcelis spp.;

from the order of the Anoplura, for example Haematopinus spp., Linognathus spp., Pediculus spp., Pemphigus spp. und Phylloxera spp.;

from the order of the Mallophaga, for example Damalinea spp. and Trichodectes spp.;

from the order of the Thysanoptera, for example Frankliniella spp., Hercinothrips spp., Taeniothrips spp., *Thrips palmi, Thrips tabaci* und *Scirtothrips aurantii*;

from the order of the Heteroptera, for example Cimex spp., *Distantiella theobroma*, Dysdercus spp., Euchistus spp., Eurygaster spp., Leptocorisa spp., Nezara spp., Piesma spp., Rhodnius spp., *Sahlbergella singularis*, Scotinophara spp. and Triatoma spp.;

from the order of the Homoptera, for example *Aleurothrixus floccosus, Aleyrodes brassicae*, Aonidiella spp., Aphididae, Aphis spp., Aspidiotus spp., *Bemisia tabaci*, Ceroplaster spp., *Chrysomphalus aonidium, Chrysomphalus dictyospermi, Coccus hesperidum*, Empoasca spp., *Eriosoma larigerum*, Erythroneura spp., Gascardia spp., Laodelphax spp., *Lecanium corni*, Lepidosaphes spp., Macrosiphus spp., Myzus spp., Nephotettix spp., Nilaparvata spp., Paratoria spp., Pemphigus spp., Planococcus spp., Pseudaulacaspis spp., Pseudococcus spp., Psylla spp., *Pulvinaria aethiopica*, Quadraspidiotus spp., Rhopalosiphum spp., Saissetia spp., Scaphoideus spp., Schizaphis spp., Sitobion spp., *Trialeurodes vaporariorum, Trioza erytreae* and *Unaspis citri*;

from the order of the Hymenoptera, for example Acromyrmex, Atta spp., Cephus spp., Diprion spp., Diprionidae, *Gilpinia polytoma*, Hoplocampa spp., Lasius spp., *Monomorium pharaonis*, Neodiprion spp., Solenopsis spp. and Vespa spp.;

from the order of the Diptera, for example Aedes spp., *Antherigona soccata, Bibio hortulanus, Calliphora erythrocephala*, Ceratitis spp., Chrysomyia spp., Culex spp., Culerebra spp., Dacus spp., *Drosophila melanogaster*, Fannia spp., Gastrophilus spp., Glossina spp., Hypoderma spp., Hyppobosca spp., Liriomyza spp., Lucilia spp., Melanagromyza spp., Musca spp., Oestrus spp., Orseolia spp., *Oscinella frit, Pegomyia hyoscyami*, Phorbia spp., *Rhagoletis pomonella*, Sciara spp., Stomoxys spp., Tabanus spp., Tannia spp. and Tipula spp.;

from the order of the Siphonaptera, for example Ceratophyllus spp., *Xenopsylla cheopis*, from the order of the Acarina, for example *Acarus siro, Aceria sheldoni, Aculus schlechtendali*, Amblyomma spp., Argas spp., Boophilus spp., Brevipalpus spp., *Bryobia praetiosa*, Calipitrimerus spp., Chorioptes spp., *Dermanyssus gallinae, Eotetranychus carpini*, Eriophyes spp., Hyalomma spp., Ixodes spp., *Olygonychus pratensis*, Ornithodoros spp., Panonychus spp., *Phyllocoptruta oleivora, Polyphagotarsonemus latus*, Psoroptes spp., Rhipicephalus spp., Rhizoglyphus spp., Sarcoptes spp., Tarsonemus spp. and Tetranychus spp.; and from the order of the Thysanura, for example *Lepisma saccharina*.

Particularly important in the case of the compounds according to the invention is the use in the control of ectoparasites which damage plants. The compounds of formula I are active against rice cicadas, for example from the families Delphacidae and Cicadellidae, such as *Nilaparvata lugens, Laodelphax striatellus* and *Nephotettix cincticeps*. The active substances of the formula I also have an excellent action against the so-called "whitefly", which is difficult to combat, of the family Aleyrodidae, genera Bemisia and Trialeurodes, such as *Bemisia tabaci* or *Trialeurodes vaporarium*. The compounds of the formula I have an excellent action against pests of fruit trees, of the Tortricidae and Olethreutidae families, with the genera Cydia, Adoxophyes and Lobesia, for example *Cydia pomonella, Adoxophyes orana* and *Lobesia botrana*.

The compounds of the formula I essentially cause an inhibition of growth in the various development stages in the target groups of pests, so that the lower infestation with pests can be accounted for by disruptions in the development of the pests, in particular by a chemosterilizing and ovicidal effect.

Compounds of the formula I which should be emphasized because of their advantageous action are those in which a) $R_2$ is a radical of the formula

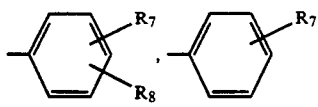

or —$C(CH_3)_2$—CN and each $R_5$ and $R_6$ radical is either fluorine or chlorine, or b) $R_2$ is a radical of the formula

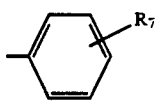

or —$C(CH_3)$—CN, $R_3$ and $R_4$ independently of one another are hydrogen or methyl, $R_5$ and $R_6$ are fluorine or chlorine, and $R_7$ is hydrogen, halogen, $C_1$-$C_4$alkyl, methoxy or nitro, or c) $R_2$ is the radical

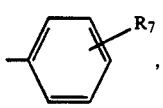

$R_3$ and $R_4$ are hydrogen, $R_5$ and $R_6$ are fluorine or chlorine, $R_7$ is hydrogen, chlorine, bromine or $C_1$-$C_4$alkyl, and n is zero or two, or d) $R_1$ is $C_1$-$C_3$alkyl, $R_2$ is

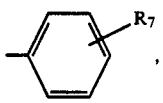

$R_3$ and $R_4$ are hydrogen, $R_7$ is hydrogen, chlorine or methyl, and n is zero.

In a preferred embodiment of present invention the group of preferred compounds of formula I consists of the compounds of the narrower formula Ia

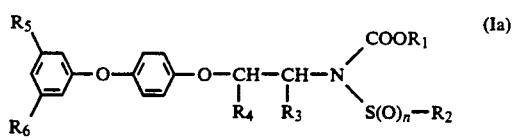

(Ia)

where $R_1$ is $C_1$-$C_4$alkyl or $C_3$-$C_4$alkenyl, $R_2$ is $C_1$-$C_4$alkyl or a radical of the formula

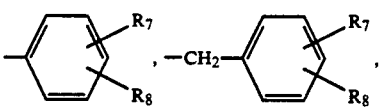

—$C(CH_3)_2$—CN or —$N(R_9)$—COO—$C_1$-$C_4$alkyl, $R_3$ and $R_4$ independently of one another are hydrogen or methyl, $R_5$ is fluorine or chlorine, $R_6$ is fluorine when $R_5$ is fluorine or is hydrogen when $R_5$ is chlorine, $R_7$ and $R_8$ independently of one another are hydrogen, halogen, $C_1$-$C_4$alkyl, $C_1$-$C_4$alkoxy or nitro, $R_9$ is $C_1$-$C_4$alkyl and n is zero, one or two.

In said narrower formula Ia the following subgroups are preferred, in which
a) $R_2$ is a radical of the formula

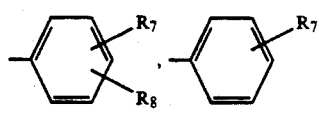

or —C(CH$_3$)$_2$—CN and $R_5$ and $R_6$ are fluorine, or
b) $R_2$ is a radical of the formula

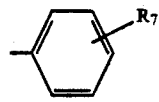

or —C(CH$_3$)—CN, $R_3$ and $R_4$ independently of one another are hydrogen or methyl, $R_5$ and $R_6$ are fluorine and $R_7$ is hydrogen, halogen, C$_1$–C$_4$alkyl, methoxy or nitro, or
c) $R_2$ is the radical

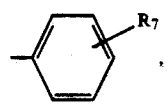

$R_3$ and $R_4$ are hydrogen, $R_5$ and $R_6$ are fluorine, $R_7$ is hydrogen, chlorine, bromine or C$_1$–C$_4$alkyl, and n is zero or two, or
d) $R_1$ is C$_1$–C$_3$alkyl, $R_2$ is

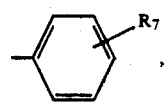

$R_3$ and $R_4$ are hydrogen, $R_7$ is hydrogen, chlorine or methyl, and n is zero.

The following individual compounds according to the present invention must be mentioned as being preferred:

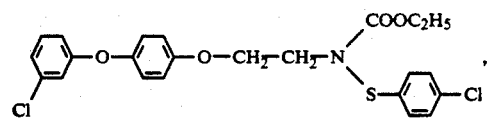

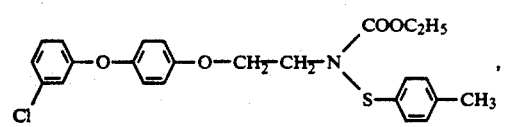

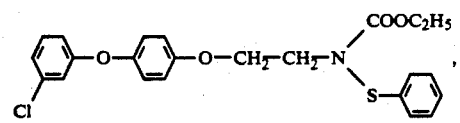

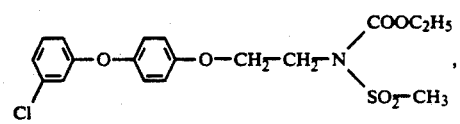

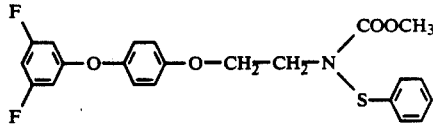

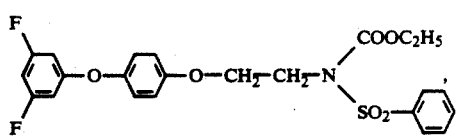

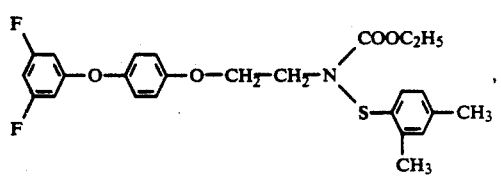

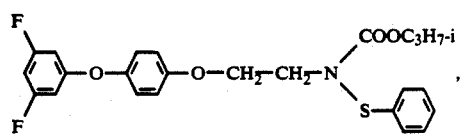

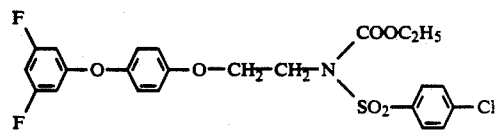

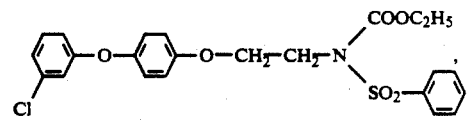

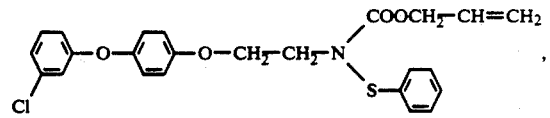

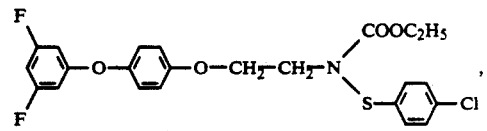

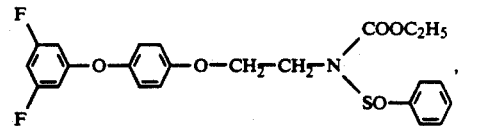

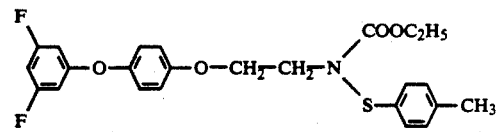

and

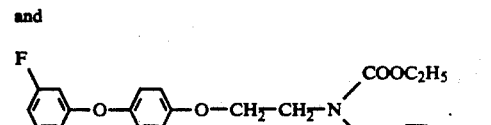

The compounds of the formula I according to the invention can be prepared by methods known per se. For example, the compounds of the formula I can be obtained either when a) a phenoxyphenol of the formula II

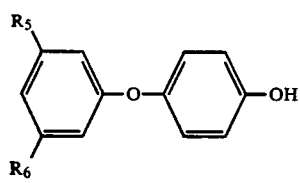  (II)

where $R_5$ and $R_6$ are as defined under formula I is reacted, in the presence of a base, with an ethylcarbamic acid derivative of the formula III

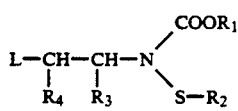  (III)

where $R_1$, $R_2$, $R_3$ and $R_4$ are as defined under formula I and L is a leaving group, for example halogen, preferably chlorine or bromine, or a sulfonyloxy group, for example methylsulfonyloxy, trifluoromethylsulfonyloxy, phenylsulfonyloxy or tolylsulfonyloxy, and the resulting product of the formula Ia

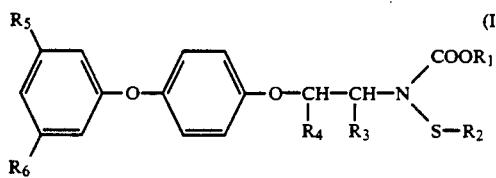  (Ia)

where $R_1$, $R_2$, $R_3$, $R_4$, $R_5$ and $R_6$ are as defined under formula I, may be oxidized to give the compounds of the formula I where n is one or two; or when b) an ethylcarbamic acid derivative of the formula IV

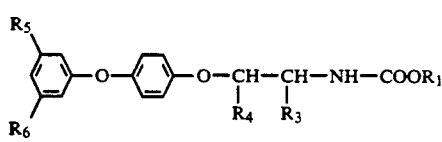  (IV)

where $R_1$, $R_3$, $R_4$, $R_5$ and $R_6$ are as defined under formula I, is reacted, in the presence of a base, with a sulfenyl halide of the formula V

  (V)

Hal-S—$R_2$ where $R_2$ is as defined under formula I and Hal is halogen, preferably chlorine, and the resulting product of the formula Ia may be oxidized to give the compounds of the formula I where n is one or two; or when c) an ethylcarbamic acid derivative of the formula IV is reacted, in the presence of a base, with a sulfinyl halide of the formula VI Hal-SO—$R_2$  (VI)

where $R_2$ is as defined under formula I and Hal is halogen, preferably chlorine, and the resulting product of the formula Ib

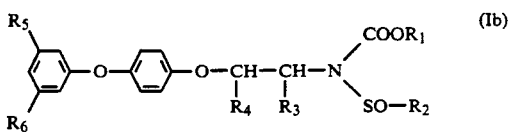  (Ib)

where $R_1$, $R_2$, $R_3$, $R_4$, $R_5$ and $R_6$ are as defined under formula I may be oxidized to give the compounds of the formula I where n is two; or when d) an ethylcarbamic acid derivative of the formula IV is reacted, in the presence of a base, with a sulfonyl halide of the formula VII Hal-SO$_2$—$R_2$  (VII)

where $R_2$ is as defined under formula I and Hal is halogen, preferably chlorine, to give a compound of the formula Ic

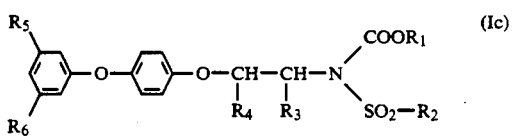  (Ic)

where $R_1$, $R_2$, $R_3$, $R_4$, $R_5$ and $R_6$ are as defined under formula I; or when e) an ethylamine derivative of the formula VIII

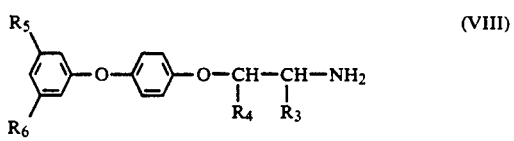  (VIII)

where $R_3$, $R_4$, $R_5$ and $R_6$ are as defined under formula I is acylated, in the presence of a base, with a haloformic acid derivative of the formula IX Hal-COOR$_1$  (IX)

where $R_1$ is as defined under formula I and Hal is halogen, preferably chlorine, and the resulting intermediate of the formula IV is sulfenylated with a sulfenic acid halide of the formula V in the presence of a base, and the resulting product of the formula Ia may be oxidized to give the compounds of the formula I where n is one or two; or when f) an ethylamine derivative of the formula VIII is sulfenated with a sulfenic acid halide of the formula V in the presence of a base and the resulting intermediate of the formula X

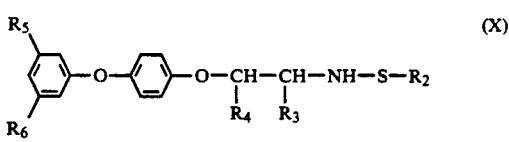  (X)

where $R_2$, $R_3$, $R_4$, $R_5$ and $R_6$ are as defined under formula I is acylated with a haloformic acid derivative of the formula IX in the presence of a base, and the resulting product of the formula Ia may be oxidized to give the compounds of the formula I where n is one or two; or when g) an alkali metal salt of the sulfonamide of the formula Xa is reacted with a haloformic acid derivative of the formula IX, $R_1$ to $R_6$ being as defined under formula I and $Me^{\oplus}$ being an alkali metal cation:

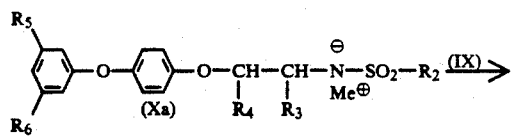

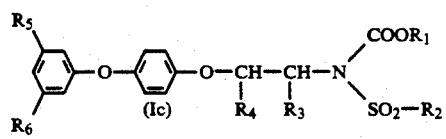

The abovementioned processes a), b), c), d), e), f) and g) can preferably be carried out under atmospheric pressure and in the presence of an inert organic solvent or diluent. Examples of suitable solvents or diluents are, depending on the type of the reaction, ether and ether-like compounds, such as dipropyl ether, dibutyl ether, dioxane, dimethoxyethane and tetrahydrofuran; N,N-dialkylated carboxamides, such as N,N-dimethylformamide, aliphatic, aromatic and halogenated hydrocarbons, in particular benzene, toluene, xylene, chloroform, methylene chloride, carbon tetrachloride and chlorobenzene; dimethyl sulfoxide, sulfolane, and also ketones, for example acetone, methyl ethyl ketone, methyl isopropyl ketone and methyl isobutyl ketone.

The reaction temperatures in these processes are generally between $-20°$ C. and the boiling point of the reaction mixture. It is preferred not to exceed an upper temperature of $+100°$ C. Preferred temperature ranges are those between $0°$ and $+50°$ C., but particularly those between $0°$ and $+40°$ C.

Suitable bases for process a) are alkali metal hydrides or alkaline earth metal hydrides, such as lithium hydride, sodium hydride or calcium hydride; alkali metal hydroxides, such as sodium hydroxide or potassium hydroxide; alkali metal carbonates, such as sodium carbonate or potassium carbonate; alcoholates, such as sodium ethylate, sodium methylate, potassium ethylate, potassium methylate or potassium tert-butylate. Tertiary amines, for example triethylamine, pyridine or diisopropylethylamine, are likewise suitable as bases. The etherification reaction can be carried out under milder conditions when the leaving group L is selected from the series of the sulfonic acid derivatives, such as methanesulfonic acid or toluenesulfonic acid, or when, in the event that L is fluorine, chlorine or bromine, catalytic amounts of alkali metal iodide are added, for example potassium iodide.

Bases in processes b), c), d), e) and f) which are preferably suitable are tertiary amines such as trialkylamines, pyridines or N,N-dialkylanilines, for example triethylamine, diisopropylethylamine, pyridine, 4-dimethylaminopyridine, dimethylaniline or diethylaniline.

In the case of liquid tertiary amines, these can be simultaneously employed in the reaction as solvents.

If it is desired to alter the oxidation level of the sulfur atoms in the compounds obtained by process a), b), c), d), e) or f), this can be effected by oxidation reactions known per se. Suitable reagents are customary oxidants under customary reaction conditions. The following may be mentioned as examples of oxidants: peracids, such as peracetic acid, performic acid, perbenzoic acid, 3-chloroperbenzoic acid or monoperphthalic acid, hydrogen peroxide, periodic acid, sodium periodate $NaIO_4$, and also alkali metal chromates. While, in typical reactions, organic peracids are reacted in chlorinated hydrocarbons, such as methylene chloride, chloroform or ethylene chloride, the solvents suitable for inorganic oxidants contain water and/or are miscible with water, such as acetone, acetic acid or formic acid. It is preferred to prepare performic acid in situ, for example by adding $H_2O_2$ to formic acid. The reaction temperatures of the oxidation mixtures are between $-20°$ C. and $+60°$ C.

The intermediates of the formulae II, IV, V, VI, VII and IX are known or can be prepared by methods known per se.

The intermediates of the formula III can alternatively be obtained in accordance with one of the following diagrams:

Diagram 1:

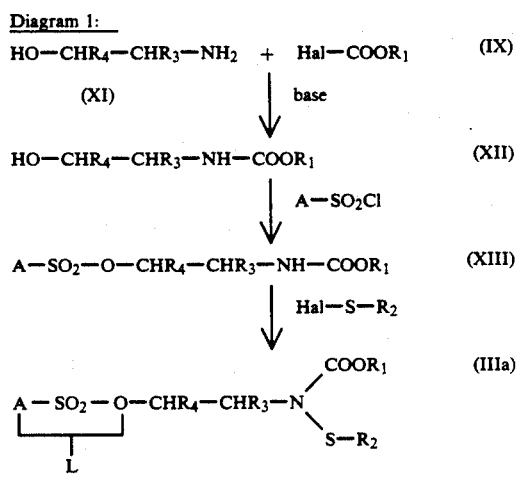

Hal: halogen, preferably chlorine,
A: organic radical, preferably $CH_3$, $CF_3$, phenyl or tolyl,
L: leaving group,
$R_1$, $R_2$, $R_3$, $R_4$, Y, Z: defined as under formula I, or Diagram 2:

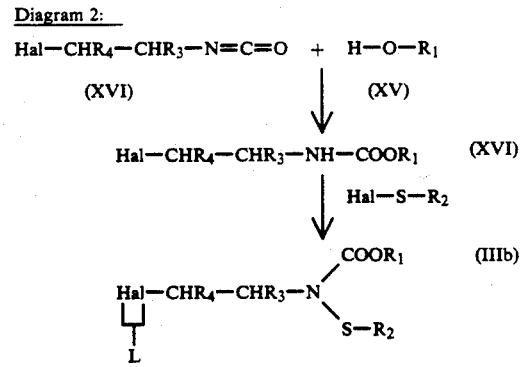

Hal: halogen, preferably chlorine,
A: organic radical, preferably $CH_3$, $CF_3$, phenyl, tolyl,
L: leaving group,
$R_1$, $R_2$, $R_3$, $R_4$: defined as under formula I.

The intermediates of the formula VIII can be prepared from the corresponding carbonyl compounds by "reductive amination":

Diagram 3:

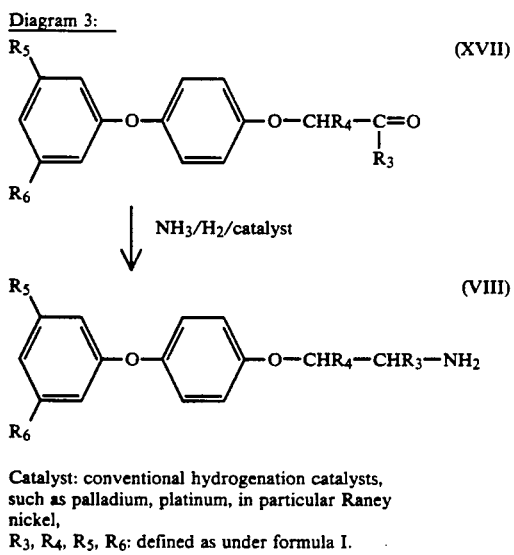

Catalyst: conventional hydrogenation catalysts, such as palladium, platinum, in particular Raney nickel,
$R_3$, $R_4$, $R_5$, $R_6$: defined as under formula I.

After the imine has been formed from XVII with ammonia, other reducing reagents can also be used in place of the reduction system $H_2$/catalyst, such as complex hydrides, for example sodium borohydride.

The reagents employed in diagrams 1, 2 and 3 are mostly known, commercially available or they can be prepared from known products by simple methods. The reaction conditions correspond to those of analogous reactions which are known.

The action of the compounds according to the invention, or of the agents containing them, can be considerably broadened and adapted to given circumstances by adding other insecticides and/or acaricides. Suitable as such additions are, for example, organophosphorus compounds, nitrophenols and their derivatives, formamidines, ureas, carbamates, pyrethroids, chlorinated hydrocarbons and preparations of *Bacillus thuringiensis*.

It is particularly advantageous to combine the compounds of the formula I with substances which bring about a more powerful pesticidal effect. Examples of such compounds are, inter alia: piperonyl butoxide, propynyl ether, propynyl oximes, propynyl carbamates and propynyl phosphonates, 2-(3,4-methylenedioxyphenoxy)-3,6,9-trioxaundecane or S,S,S-tributyl phosphorotrithioate.

The compounds of the formula I are employed in unaltered form or, preferably, together with agrochemically acceptable auxiliaries conventionally used in the art of formulation, and they are therefore processed in a known manner to give, for example, emulsion concentrates, directly sprayable or dilutable solutions, dilute emulsions, wettable powders, soluble powders, dusts, granules, and also encapsulations, for example in polymeric substances. The application methods, such as spraying, misting, atomizing, scattering or pouring, as well as the agents are selected to suit the intended aims and the prevailing circumstances.

The formulations, i.e. the agents, preparations or compositions containing the active substance of the formula I or combinations of these active substances, insecticides or acaricides, and, if desired, a solid or liquid additive, are prepared in a known manner, for example by intimately mixing and/or grinding the active substances with extenders, for example with solvents, solid carriers, and, if desired, surface-active compounds (surfactants).

The following are possible as solvents: aromatic hydrocarbons, preferably the fractions $C_8$-$C_{12}$, for example xylene mixtures or substituted naphthalenes, phthalic esters, such as dibutyl phthalate or dioctyl phthalate, aliphatic hydrocarbons, such as cyclohexane, paraffins, alcohols and glycols as well as their ethers and esters, such as ethanol, ethylene glycol, ethylene glycol monomethyl ether or ethylene glycol monoethyl ether, ketones, such as cyclohexanone, strongly polar solvents, such as N-methyl-2-pyrrolidone, dimethyl sulfoxide or dimethylformamide, and also epoxidized or unepoxidized vegetable oils, such as epoxidized coconut oil or soya oil, or water.

Solid carriers which are generally used, for example for dusts and dispersible powders, are ground natural minerals, such as calcite, talc, kaolin, montmorillonite or attapulgite. To improve the physical properties, it is also possible to add highly-disperse silicas or highly-disperse absorptive polymers.

Possible particulate, adsorptive carriers for granules are either porous types, for example pumice, brick grit, sepiolite or bentonite, and also non-sorptive carrier materials, such as calcite or sand. Moreover, a large number of pregranulated materials of inorganic or organic nature can be used, such as, in particular, dolomite or communicated plant residues.

Suitable surface-active compounds are non-ionic, cationic and/or anionic surfactants having good emulsifying, dispersing and wetting properties, depending on the nature of the active substance of the formula I to be formulated or on the combination of these active substances and other insecticides or acaricides. Surfactants are also to be understood as meaning mixtures of surfactants.

Anionic surfactants which are suitable can be either so-called water-soluble soaps or water-soluble synthetic surface-active compounds.

Suitable soaps are the alkali metal salts, alkaline earth metal salts or substituted or unsubstituted ammonium salts of higher fatty acids ($C_{10}$-$C_{22}$), such as the sodium salts or potassium salts of oleic or stearic acid, or of natural mixtures of fatty acids which can be obtained, for example, from coconut or tallow oil. Mention must also be made of the fatty acid methyltaurinates.

However, so-called surfactants are used more frequently, in particular fatty sulfonates, fatty sulfates, sulfonated benzimidazole derivatives or alkylarylsulfonates.

The fatty sulfonates or fatty sulfates are generally in the form of alkali metal salts, alkaline earth metal salts or substituted or unsubstituted ammonium salts, and generally have an alkyl radical having 8 to 22 C atoms, alkyl also including the alkyl moiety of acyl radicals, for example the Na or calcium salt of ligninsulfonic acid, of the dodecylsulfuric ester or of a fatty alcohol sulfate mixture prepared from natural fatty acids. This group also includes the salts of the sulfuric esters and sulfonic acids of fatty alcohol/ethylene oxide adducts. The sulfonated benzimidazole derivatives preferably contain 2 sulfonyl groups and one fatty acid radical having about 8-22 C atoms. Examples of arylalkylsulfonates are the Na, Ca or triethanolamine salts of dodecylbenzenesulfonic acid, of dibutylnaphthalenesulfonic acid or of a naphthalenesulfonic acid/formaldehyde condensation product. Other suitable compounds are the corresponding phosphates, such as the salts of the phosphoric ester of a p-nonylphenol/(4–14)-ethylene oxide adduct.

Suitable non-ionic surfactants are mainly polyglycol ether derivatives of aliphatic or cycloaliphatic alcohols, saturated or unsaturated fatty acids and alkylphenols, which can contain 3 to 30 glycol ether groups and 8 to 20 carbon atoms in the (aliphatic) hydrocarbon radical and 6 to 18 carbon atoms in the alkyl radical of the alkylphenols. Other non-ionic surfactants which are suitable are the water-soluble polyethylene oxide adducts with polypropylene glycol, ethylenediaminopolypropylene glycol and alkylpolypropylene glycol which have 1 to 10 carbon atoms in the alkyl chain and which contain 20 to 250 ethylene glycol ether groups and 10 to 100 propylene glycol ether groups. The abovementioned compounds customarily contain 1 to 5 ethylene glycol units per propylene glycol unit.

Examples of non-ionic surfactants which may be mentioned are nonylphenolpolyethoxyethanols, castor oil polyglycol ethers, polypropylene/polyethylene oxide adducts, tributylphenoxypolyethoxyethanol, polyethylene glycol and octylphenoxypolyethoxyethanol. Other suitable substances are fatty acid esters of polyoxyethylenesorbitan, such as polyoxyethylenesorbitan trioleate.

The cationic surfactants are mainly quaternary ammonium salts, which contain at least one alkyl radical having 8 to 22 C atoms as N-substituent and which have lower halogenated or free alkyl, benzyl or lower hydroxyalkyl radicals as further substituents. The salts are preferably in the form of halides, methylsulfates or ethylsulfates, for example stearyltrimethylammonium chloride or benzyldi(2-chloroethyl)ethylammonium bromide.

The surfactants customary in the art of formulation are described, inter alia, in the following publications:
"1985 International McCutcheon's Emulsifiers & Detergents", Glen Rock NJ USA, 1985",
H. Stache, "Tensid-Taschenbuch [Surfactant Guide]", 2nd edition, C. Hanser Verlag Munich, Vienna 1981,
M. and J. Ash. "Encyclopedia of Surfactants", vol. I–III, Chemical Publishing Co., New York, 1980–1981.

As a rule, the pesticidal preparations contain 0.1 to 99%, in particular 0.1 to 95%, of the active substance of the formula I or combinations of this active substance with other insecticides or acaricides, 1 to 99.9% of a solid or liquid additive and 0 to 25%, in particular 0.1 to 20%, of a surfactant. While concentrated agents are often preferred as commercially available goods, the end user generally uses dilute preparations containing considerably lower concentrations of active substance. Typical application concentrations are between 0.1 and 1,000 ppm, preferably between 0.1 and 500 ppm. The application rates per hectare are generally 10 to 1,000 g of active substance per hectare, preferably 25 to 250 g/ha.

In particular, preferred formulations have the following composition: (%=percent by weight)

| Emulsifiable concentrates | | |
|---|---|---|
| Active ingredient: | 1 to 20%, | 5 to 10% being preferred |
| Surface-active agent: | 5 to 30%, | preferably 10 to 20% |
| Liquid carrier: | 50 to 94%, | preferably 70 to 85% |
| Dusts: | | |
| Active ingredient: | 0.1 to 10%, | preferably 0.1 to 1% |
| Solid carrier: | 99.9 to 90%, | preferably 99.9 to 99% |
| Suspension concentrates: | | |
| Active ingredient: | 5 to 75%, | preferably 10 to 50% |
| Water: | 94 to 24%, | preferably 88 to 30% |
| Surface-active agent: | 1 to 40%, | preferably 2 to 30% |
| Wettable powders: | | |
| Active ingredient: | 0.5 to 90%, | preferably 1 to 80% |
| Surface-active agent: | 0.5 to 20%, | preferably 1 to 15% |
| Solid carrier material: | 5 to 95%, | preferably 15 to 90% |
| Granules: | | |
| Active ingredient: | 0.5 to 30%, | preferably 3 to 15% |
| Solid carrier: | 99.5 to 70%, | preferably 97 to 85% |

The agents can also contain further additions, such as stabilizers, defoamers, preservatives, viscosity regulators, binders, tackifiers and also fertilizers or other active substances for achieving specific effects.

The examples which follow are intended to illustrate the invention. They do not restrict the invention.

EXAMPLE H1

Ethyl N-phenylthio-2-[4-(3,5-difluorophenoxy)phenoxy]ethylcarbamate

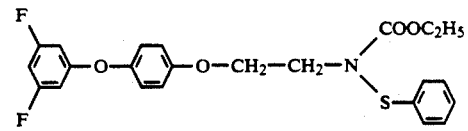

a) 27.6 g of finely pulverulent potassium carbonate and 1.0 g of pulverized potassium iodide are added to a solution of 22.2 g of 4-(3,5-difluorophenoxy)phenol in 80 ml of dimethylformamide. 18.2 g of ethyl 2-chloroethylcarbamate are furthermore added dropwise, and the reaction mixture is heated for 16 hours at +95° C., with stirring. The reaction mixture is then filtered, the filtrate is poured into 400 ml of water, and the mixture is extracted three times using diethyl ether. The combined organic phases are washed with water and dried over sodium sulfate, and the solvent is distilled off. The residue is purified over silica gel (eluent: n-hexane/diethyl ether, 3:1), which gives pure ethyl 2-[4-(3,5-difluorophenoxy)phenoxy]ethylcarbamate as a colourless solid of melting point 54°–56° C., which solidifies in crystalline form; yield: 92% of theory.

b) 5.7 g of freshly distilled phenylsulfenyl chloride in 10 ml of toluene are added dropwise at 0° to +5° C. in the course of 30 minutes to a solution of 12 g of ethyl 2-[4-(3,5-difluorophenoxy)phenoxy]ethylcarbamate in 40 ml of pyridine, with stirring. After this, the mixture is stirred for 4 more hours at room temperature. The reaction mixture is poured into 300 ml of 2N hydrochloric acid and ice, and the mixture is extracted twice using diethyl ether. The combined organic phases are washed to neutrality with water and sodium chloride solution and dried over sodium sulfate. The solvent is distilled off in vacuo, and the residue is purified by chromatography on silica gel (eluent: hexane/diethyl ether, 20:1), which gives pure ethyl N-phenylthio-2-[4-(3,5-difluorophenoxy)phenoxy]ethylcarbamate, $n_D^{20}$: 1.5700.

EXAMPLE H2

Ethyl N-(4-chlorophenylthio)-2-[4-(3,5-difluorophenoxy)-phenoxy]ethylcarbamate

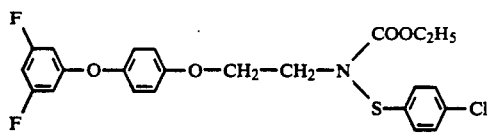

7.6 g of freshly distilled 4-chlorophenylsulfenyl chloride is added dropwise at 0° to +5° C. in the course of 30 minutes to a solution of 12 g of ethyl 2-[4-(3,5-difluorophenoxy)phenoxy]ethylcarbamate in 40 ml of pyridine, with stirring. After this, the mixture is stirred for 16 more hours at room temperature. The reaction mixture is poured into 200 ml of 2N hydrochloric acid and ice, and the mixture is extracted twice using diethyl ether. The combined ether extracts are washed to neutrality with water and dried over sodium sulfate. The solvent is distilled off in vacuo, and the residue is purified by chromatography on silica gel (eluent: hexane/diethyl ether, 9:1), which gives pure ethyl N-(4-chlorophenylthio)-2-[4-(3,5-difluorophenoxy)phenoxy]ethylcarbamate, $n_D^{20}$ 1.5763.

EXAMPLE H3

Ethyl N-phenylthio-2-[4-(3,5-difluorophenoxy)phenoxy]ethylcarbamate

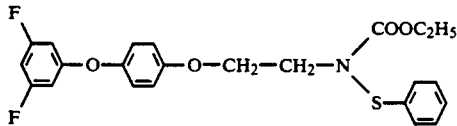

a) 60 g of methanesulfonyl chloride are metered over approximately 30 minutes at 0° to +5° C. to a solution of 66.5 g of ethyl 2-hydroxyethylcarbamate, 43.5 g of pyridine and 1.9 g of 4-dimethylaminopyridine in 150 ml of methylene chloride, with stirring, and the mixture is stirred for 2 more hours at +5° C. and then for 16 hours at room temperature. The reaction mixture is filtered, the residue is washed with a small quantity of ethyl acetate, and the combined filtrates are washed with dilute hydrochloric acid and water. After the mixture has been dried over magnesium sulfate, the solvent mixture is removed completely by distillation in vacuo, which gives ethyl 2-methylsulfonyloxyethylcarbamate, $n_D^{20}$ 1.4450.

b) 21.1 g of ethyl 2-methanesulfonyloxyethylcarbamate, obtained as above, and 0.4 g of 4-dimethylaminopyridine are dissolved in 48 g of pyridine, and 15.8 g of freshly distilled phenylsulfenyl chloride in 15 ml of toluene are added dropwise in the course of 20 minutes at 0° to +5° C., with stirring. The mixture is stirred at this temperature for 4 more hours. After this, the reaction mixture is poured into 300 g of ice and 200 ml of 2N hydrochloric acid, and the mixture is extracted several times with ether. The combined organic phases are washed to neutrality with saturated sodium chloride solution and dried over sodium sulfate. The solvent is distilled off in vacuo. Chromatographic purification on silica gel (eluent: diethyl ether/hexane, 1:1) gives pure ethyl N-phenylthio-2-methylsulfonyloxyethylcarbamate, $n_D^{20}$: 1.5390.

c) A solution of the sodium salt of 4-(3,5-difluorophenoxy)phenol (prepared from 4.3 g of 4-(3,5-difluorophenoxy)phenol and 0.8 g of a 55% dispersion of sodium hydride in mineral oil in 40 ml of dry dimethyl sulfoxide) is metered at a constant rate at +25° C. in the course of 5 hours to a solution of 6.5 g of ethyl N-phenylthio-2-methylsulfonyloxyethylcarbamate and 0.1 g of hydroquinone in 20 ml of anhydrons dimethyl sulfoxide, with stirring. The mixture is stirred for 5 more hours at room temperature. After this, the reaction mixture is poured into ice-water and extracted repeatedly with an ether/hexane mixture (1:4), and the combined organic phases are washed with water and dried over sodium sulfate. After the solvents have been distilled off in vacuo, the crude product is purified by chromatography, by which process ethyl N-phenylthio-2-[4-(3,5-difluorophenoxy)phenoxy]ethylcarbamate is isolated, $n_D^{20}$: 1.5700.

EXAMPLE H4

Ethyl N-phenylthio-2[4-(3,5-fluorophenoxy)phenoxy]ethylcarbamate

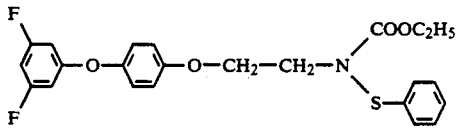

A solution of the potassium salt of 4-(4-fluorophenoxy)phenol (prepared from 4.3 g of 4-(3,5-difluorophenoxy)phenol and 2.04 g of potassium tert-butylate in 35 ml of dry dimethyl sulfoxide) is metered at a uniform rate at +25° C. in the course of 5 hours to a solution of 5.8 g of ethyl N-phenylthio-2-chloroethylcarbamate, 0.1 g of potassium iodide and 0.2 g of hydroquinone in 20 ml of anhydrous dimethyl sulfoxide, with stirring. The mixture is stirred for 5 more hours at room temperature. After this, the reaction mixture is poured into ice-water and extracted repeatedly with an ether/hexane mixture (1:4). The combined organic phases are washed with water and dried over sodium sulfate. After the solvents have been distilled off in vacuo, the crude product is purified by chromatography, by which process ethyl N-phenylthio-2-[4-(3,5-difluorophenoxy)phenoxy]ethylcarbamate is isolated, $n_D^{20}$: 1.5700.

EXAMPLE H5

Ethyl N-phenylthio-2-[4-(3,5-difluorophenoxy)phenoxy]ethylcarbamate

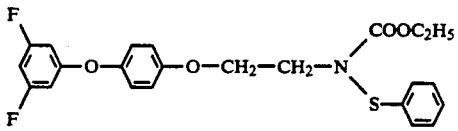

A solution of 4.3 g of 4-(3,5-difluorophenoxy)phenol and 1.58 g of pyridine or 2.58 g of ethyl diisopropylamine in 35 ml of dry dimethyl sulfoxide is metered at a constant rate at +25° C. in the course of 5 hours to a solution of 6.4 g of ethyl N-phenylthio-2-methylsulfonyloxyethylcarbamate and 0.2 g of hydroquinone in 20 ml of anhydrous dimethyl sulfoxide, with stirring. The mixture is stirred for 5 more hours at room temperature. After this, the reaction mixture is poured into ice-water and extracted three times with an ether/hexane mixture (1:4), and the combined organic phases are washed with water and dried over sodium sulfate. After the solvents have been distilled off in vacuo, the crude product is purified by chromatography, by which process ethyl N-phenylthio-2-[4-(3,5-difluorophenoxy)-phenoxy]ethylcarbamate is isolated, $n_D^{20}$ 1.5700.

EXAMPLE H6

Ethyl N-phenylsulfinyl-2-[4-(3,5-difluorophenoxy)phenoxy]ethylcarbamate

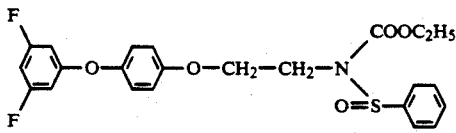

A solution of 8.1 g of 55% 3-chloroperbenzoic acid in 50 ml of dichloromethane is added dropwise at 0° to +5° C. in the course of 20 minutes to a solution of 11.5 g of ethyl N-phenylthio-2-[4-(3,5-difluorophenoxy)-phenoxy]ethylcarbamate in 80 ml of dichloromethane, with stirring. After the reaction mixture has been stirred for 2 hours at +20° to +22° C., it is extracted twice with a 10% sodium carbonate solution and washed to neutrality with water. The dichloromethane phase is dried over sodium sulfate, and the solvent is distilled off in vacuo. The residue is purified by chromatography on silica gel (eluent: n-hexane/diethyl ether, 3:1), which process gives ethyl N-phenylsulfinyl-2-[4-(3,5-difluorophenoxy)phenoxy]ethylcarbamate, colourless viscous oil $n_D^{20}$:1.5645.

EXAMPLE H7

Ethyl N-phenylsulfonyl-2-[4-(3,5-difluorophenoxy)phenoxy]ethylcarbamate

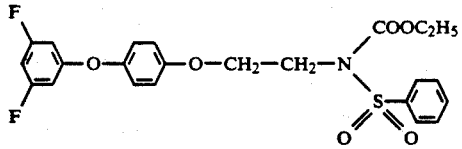

A solution of 4.0 g of 55% 3-chloroperbenzoic acid in 30 ml of dichloromethane is added dropwise at about +5° C. in the course of 10 minutes to a solution of 4.8 g of ethyl N-phenylsulfinyl-2-[4-(3,5-difluorophenoxy)-phenoxy]ethylcarbamate in 30 ml of dichloromethane, with stirring. The reaction mixture is stirred for 16 hours at room temperature and then washed twice with 10% sodium carbonate solution and then to neutrality with water. The organic phase is dried over magnesium sulfate, and the solvent is distilled off in vacuo. The crude product is purified further by chromatography on silica gel (eluent: n-hexane/diethyl ether, 3:1), by which process ethyl N-phenylsulfonyl-2-[4-(3,5-difluorophenoxy)phenoxy]ethylcarbamate is isolated as a colourless resinous substance, $n_D^{20}$: 1,5610.

EXAMPLE H8

Ethyl N-methylsulfonyl-2-[4-(3-chlorophenoxy)phenoxy]ethylcarbanate

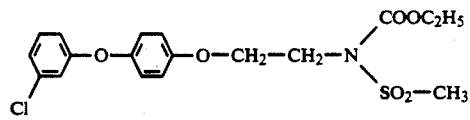

1.47 g of a 55% dispersion of sodium hydride in mineral oil are washed repeatedly with n-hexane and suspended in 30 ml of tetrahydrofuran. A solution of 11.3 g of ethyl 2-[4-(3-chlorophenoxy)phenoxy]ethylcarbamate (m.p. 45°-46° C.; prepared from 4-(3-chlorophenoxy)phenol and ethyl 2-chloroethylcarbamate in dimethylformamide analogously to Example H1a) in 30 ml of tetrahydrofuran is added dropwise at room temperature to this suspension with stirring, and the mixture is stirred for about 5 hours at room temperature until the reaction of the sodium hydride is complete. After this, a solution of 4.2 g of methanesulfonyl chloride in 10 ml of tetrahydrofuran is added dropwise at 0°-5° C. in the course of 10 minutes, and the mixture is stirred for 15 more hours at room temperature. The reaction mixture is now poured into ice-water and extracted repeatedly with ether. The combined ether phases are washed repeatedly with 5% sodium carbonate solution and then with water, the organic phase is dried over sodium sulfate and the solvent is distilled off. The crude product is purified further by chromatography on silica gel (eluent: n-hexane/diethyl ether, 5:1), by which process ethyl N-methylsulfonyl-2-[4-(3-chlorophenoxy)phenoxy]ethylcarbamate is obtained as a colourless, viscous oil, $n_D^{21}$: 1.5573.

Analogously, ethyl N-phenylsulfonyl-2-[4-(3-chlorophenoxy)phenoxy]ethylcarbamate is obtained from ethyl 2-[4-(3-chlorophenoxy)phenoxy]ethylcarbamate and benzenesulfonyl chloride as a colourless, viscous oil, $n_D^{20}$: 1.5790.

EXAMPLE H9

Methyl N-phenylthio-2-[4-(3,5-difluorophenoxy)phenoxy]ethylcarbamate

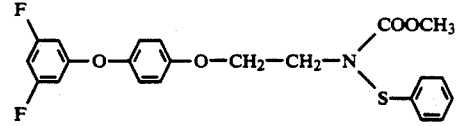

a) 21.3 g of potassium carbonate powder, 1.5 g of pulverized potassium iodide and 16 g of methyl 2-chloroethylcarbamate are added to a solution of 17.1 g of 4-(3,5-difluorophenoxy)phenol in 100 ml of dimethylformamide, and the reaction mixture is heated for 16 hours at 95° C. The cooled reaction mixture is then poured into ice-water, and the mixture is extracted repeatedly with diethyl ether. The combined ether phases are washed with water and dried over sodium sulfate, and the solvent is distilled off. The crude product is chromatographed on silica gel (eluent: n-hexane/diethyl ether, 5:1), by which process pure methyl 2-[4-(3,5-difluorophenoxy)phenoxy]ethylcarbamate is obtained, $n_D^{21}$: 1.5394.

Analogously, the following are obtained from isopropyl 2-chloroethylcarbamate, allyl 2-chloroethylcarbamate and 4-(3,5-difluorophenoxy)phenol: isopropyl 2-[4-(3,5-difluorophenoxy)phenoxy]ethylcarbamate, $n_D^{21}$: 1.5243 and allyl 2-[4-(3-chlorophenoxy)phenoxy]ethylcarbamate, m.p. 51°-52° C.

b) Analogously to the procedure of Example H1b), the following active substances according to the invention are obtained from the carbamic esters obtained in a) by reacting them with phenylsulfenyl chloride:

Methyl N-phenylthio-2-[4-(3,5-difluorophenoxy)phenoxy]ethylcarbamate, $n_D^{20}$: 1.5750;

isopropyl N-phenylthio-2-[4-(3,5-difluorophenoxy)phenoxy]ethylcarbamate, $n_D^{20}$: 1.5638 and allyl N-phenylthio-2-[4-(3-chlorophenoxy)phenoxy]ethylcarbamate, $n_D^{20}$: 1.6079.

EXAMPLE H10

Ethyl N-phenylthio-2-[4-(3-chlorophenoxy)phenoxy]-1-methylethylcarbamate

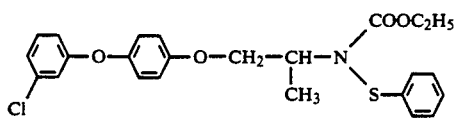

a) 32.5 g of anhydrous potassium carbonate powder and 2 g of finely pulverized potassium iodide are added to a solution of 39.8 g of 4-(3-chlorophenoxy)phenol in 250 ml of ethyl methyl ketone, and the mixture is heated to reflux temperature. 25 g of freshly distilled chloroacetone are now added dropwise in the course of 45 minutes, and the mixture is stirred for 2 more hours at reflux temperature. When the reaction mixture has cooled down, it is filtered, the solvent is distilled off in vacuo, and the residue is freed completely from the solvent in a high vacuum at 40° C. The resulting oily 4-(3-chlorophenoxy)phenoxypropanone, $n_D^{20}$: 1.5788, analytical grade, is directly reacted further.

b) In a stirred autoclave, 51 g of 4-(3-chlorophenoxy)phenoxypropanone are dissolved in 510 ml of methanol. 31 g of liquid ammonia are forced in, and the mixture is subjected to reductive amination at 40°-45° C. for 3 hours in the presence of 10 g of Raney nickel and 50 bar of hydrogen pressure. After the pressure in the autoclave has been let down, the Raney nickel is filtered off from the reaction mixture. The catalyst is washed with methanol, and the methanol is finally distilled off from the reaction mixture. The residue is chromatographed on silica gel (eluent: diethyl ether/methanol, 5:1), by which process pure 1-[4-(3-chlorophenoxy)phenoxy]-2-aminopropane is obtained, $n_D^{20}$: 1.5743.

c) 13.5 g of ethyl chloroformate are added dropwise at 20° C. in the course of 30 minutes to a solution of 31.5 g of 1-[4-(3-chlorophenoxy)phenoxy]-2-aminopropane, 20 g of diisopropylethylamine and 1 g of 4-dimethylaminopyridine in 120 ml of toluene, with stirring and slight external cooling, and the mixture is stirred for a further 15 hours at 20° C. After this, the reaction mixture is poured into 200 ml of 2N hydrochloric acid and ice-water, and the toluene phase is separated off. The aqueous phase is re-extracted with ether, the combined organic phases are washed to neutrality with water and sodium chloride solution and dried over sodium sulfate, and the solvents are distilled off in vacuo. The crude product is chromatographed on silica gel (eluent: n-hexane/diethyl ether, 5:1), by which process pure ethyl 2-[4-(3-chlorophenoxy)phenoxy]-1-methylethylcarbamate is obtained as a pale yellow oil, $n_D^{21}$: 1.5530.

d) A solution of 4 g of phenylsulfenyl chloride in 10 ml of toluene is added dropwise at 0°-5° C. in the course of 20 minutes to a solution of 9 g of ethyl 2-[4-(3-chlorophenoxy)phenoxy]-1-methylethylcarbamate in 30 ml of pyridine, with stirring, and the mixture is stirred for a further 15 hours at room temperature. Most of the pyridine and toluene is then distilled off in vacuo at a temperature of lower than 45° C., and the residue is poured into 300 ml of ice-water and extracted repeatedly with ether. The combined ether phases are first washed with cold, dilute hydrochloric acid and then with water, the mixture is dried over sodium sulfate, and the solvent is distilled off completely. The residue is purified further by chromatography on silica gel (eluent: n-hexane/diethyl ether, 19:1), by which process ethyl N-phenylthio-2-[4-(3-chlorophenoxy)phenoxy]-1-methylethylcarbamate is obtained as a colourless oil, $n_D^{20}$: 1.5810.

The following active substances of the formula I can be obtained analogously:

TABLE 1

| Comp No. | $R_1$ | $R_2$ | n | $R_3$ | $R_4$ | $R_5$ | $R_6$ | Physical data |
|---|---|---|---|---|---|---|---|---|
| 1.01 | $C_2H_5$ | $C_6H_5$ | 0 | H | H | F | F | $n_D^{20}$: 1.5700 |
| 1.02 | $C_2H_5$ | $C_6H_5$ | 1 | H | H | F | F | $n_D^{20}$: 1.5645 |
| 1.03 | $C_2H_5$ | $C_6H_5$ | 2 | H | H | F | F | $n_D^{20}$: 1.5610 |
| 1.04 | $C_2H_5$ | 4-Cl—$C_6H_4$— | 0 | H | H | F | F | $n_D^{20}$: 1.5763 |
| 1.05 | $C_2H_5$ | 4-$CH_3$—$C_6H_4$— | 0 | H | H | F | F | $n_D^{20}$: 1.5705 |
| 1.06 | $C_2H_5$ | 3-$CH_3$—$C_6H_4$— | 0 | H | H | F | F | |
| 1.07 | $C_2H_5$ | 2-$CH_3$—$C_6H_4$— | 0 | H | H | F | F | |
| 1.08 | $C_2H_5$ | 3-Cl—$C_6H_4$— | 0 | H | H | F | F | |
| 1.09 | $C_2H_5$ | 3-Cl-4-Cl—$C_6H_4$— | 0 | H | H | F | F | |
| 1.10 | $C_2H_5$ | 4-$NO_2$—$C_6H_4$— | 0 | H | H | F | F | |
| 1.11 | $C_2H_5$ | $C_6H_5$—$CH_2$— | 0 | H | H | F | F | |
| 1.12 | $CH_3$ | $C_6H_5$ | 0 | H | H | F | F | $n_D^{20}$: 1.5750 |
| 1.13 | $C_4H_9$-n | $C_6H_5$ | 0 | H | H | F | F | |

TABLE 1-continued

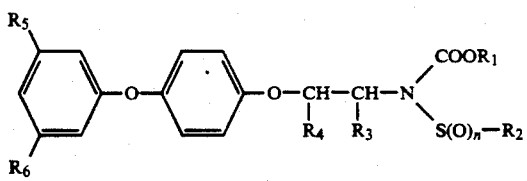

| Comp No. | R₁ | R₂ | n | R₃ | R₄ | R₅ | R₆ | Physical data |
|---|---|---|---|---|---|---|---|---|
| 1.14 | $C_2H_5$ | $C_6H_5$ | 0 | $CH_3$ | H | Cl | H | $n_D^{20}$: 1.5810 |
| 1.15 | $C_2H_5$ | $C_6H_5$ | 1 | $CH_3$ | H | F | F | |
| 1.16 | $C_2H_5$ | $C_6H_5$ | 1 | H | H | F | F | |
| 1.17 | $C_2H_5$ | $4\text{-}CH_3\text{-}C_6H_4\text{-}$ | 1 | H | H | F | F | |
| 1.18 | $C_2H_5$ | $C_6H_5$ | 0 | H | H | F | H | |
| 1.19 | $C_2H_5$ | $4\text{-}Cl\text{-}C_6H_4\text{-}$ | 0 | H | H | F | H | |
| 1.20 | $C_2H_5$ | $C_6H_5\text{-}CH_2\text{-}$ | 0 | H | H | F | H | |
| 1.21 | $C_2H_5$ | $C_6H_5$ | 1 | H | H | F | H | |
| 1.22 | $C_2H_5$ | $C_6H_5$ | 0 | H | H | Cl | H | $n_D^{21}$: 1.5851 |
| 1.23 | $C_2H_5$ | $C_6H_5$ | 1 | H | H | Cl | H | |
| 1.24 | $C_2H_5$ | $4\text{-}Cl\text{-}C_6H_4\text{-}$ | 0 | H | H | Cl | H | $n_D^{20}$: 1.5879 |
| 1.25 | $C_2H_5$ | $4\text{-}CH_3\text{-}C_6H_4\text{-}$ | 0 | H | H | Cl | H | $n_D^{20}$: 1.5934 |
| 1.26 | $C_2H_5$ | $4\text{-}CH_3\text{-}C_6H_4\text{-}$ | 0 | H | H | Cl | Cl | |
| 1.27 | $C_2H_5$ | $4\text{-}Cl\text{-}C_6H_4\text{-}$ | 0 | H | H | Cl | Cl | |
| 1.28 | $C_2H_5$ | $C_6H_5$ | 0 | H | H | Cl | Cl | |
| 1.29 | $C_2H_5$ | $C_6H_5$ | 1 | H | H | Cl | Cl | |
| 1.30 | $C_2H_5$ | $C_6H_5$ | 0 | $(CH_2)_4$ | | Cl | Cl | |
| 1.31 | $C_2H_5$ | $2\text{-}CH_3\text{-}4\text{-}CH_3\text{-}C_6H_3\text{-}$ | 0 | H | H | F | F | $n_D^{20}$: 1.5713 |
| 1.32 | $C_2H_5$ | $CH_3$ | 2 | H | H | Cl | H | $n_D^{21}$: 1.5573 |
| 1.33 | $C_3H_7\text{-}i$ | $C_6H_5$ | 0 | H | H | F | F | $n_D^{20}$: 1.5638 |
| 1.34 | $C_2H_5$ | $4\text{-}Cl\text{-}C_6H_4\text{-}$ | 2 | H | H | F | F | $n_D^{22}$: 1.5641 |
| 1.35 | $C_2H_5$ | $C_6H_5$ | 2 | H | H | Cl | H | $n_D^{20}$: 1.5790 |
| 1.36 | $\text{-}CH_2CH=CH_2$ | $C_6H_5$ | 0 | H | H | Cl | H | $n_D^{20}$: 1.6079 |
| 1.37 | $C_2H_5$ | $C_6H_5$ | 0 | $CH_3$ | H | F | F | |

FORMULATION EXAMPLES OF LIQUID ACTIVE SUBSTANCES OF THE FORMULA I (%=PERCENT BY WEIGHT)

| F1. Emulsion concentrates | a) | b) | c) |
|---|---|---|---|
| Active substance No. 1.01 | 25% | 40% | 50% |
| Ca dodecylbenzenesulfonate | 5% | 8% | 6% |
| Castor oil polyethylene glycol ether (36 mol of EO) | 5% | — | — |
| Tributylphenol polyethylene glycol ether (30 mol of EO) | — | 12% | 4% |
| Cyclohexanone | — | 15% | 20% |
| Xylene mixture | 65% | 25% | 20% |

Emulsions of any desired concentration can be prepared from such concentrates by diluting them with water.

| F2. Solutions | a) | b) | c) | d) |
|---|---|---|---|---|
| Active substance No. 1.02 | 80% | 10% | 5% | 95% |
| Ethylene glycol monomethyl ether | 20% | — | — | — |
| Polyethylene glycol MW 400 | — | 70% | — | — |
| N-Methyl-2-pyrrolidone | — | 20% | — | — |
| Epoxidized coconut oil | — | — | 1% | 5% |
| Petroleum ether (boiling range 160-190° C.) | — | — | 94% | — |

The solutions are suitable for use in the form of minute droplets.

| F3. Granules | a) | b) |
|---|---|---|
| Active substance No. 1.02 | 5% | 10% |
| Kaolin | 94% | — |
| Highly-disperse silica | 1% | — |
| Attapulgite | — | 90% |

The active substance is dissolved in methylene chloride, the solution is sprayed onto the carrier and the solvent is then evaporated off in vacuo.

| F4. Dusts | a) | b) |
|---|---|---|
| Active substance No. 1.01 | 2% | 5% |
| Highly-disperse silica | 1% | 5% |
| Talc | 97% | — |
| Kaolin | — | 90% |

Ready-to-use dusts are obtained by intimately mixing the carriers with the active substance.

FORMULATION EXAMPLES OF SOLID ACTIVE SUBSTANCES OF THE FORMULA I (%=PERCENT BY WEIGHT)

| F5. Wettable powder | a) | b) | c) |
|---|---|---|---|
| Active substance 1.03 | 25% | 50% | 75% |
| Na ligninsulfonate | 5% | 5% | — |
| Na laurylsulfate | 3% | — | 5% |
| Na diisobutylnaphthalenesulfonate | — | 6% | 10% |
| Octylphenol polyethylene glycol ether (7-8 mol of EO) | — | 2% | — |
| Highly-disperse silica | 5% | 10% | 10% |
| Kaolin | 62% | 27% | — |

The active substance is mixed thoroughly with the additives, and the mixture is ground thoroughly in a suitable mill. Wettable powders which can be diluted with water to give suspensions of any desired concentration are obtained.

| F6. Emulsion concentrate | |
| --- | --- |
| Active substance No. 1.03 | 10% |
| Octylphenol polyethylene glycol ether (4–5 mol of EO) | 3% |
| Ca dodecylbenzenesulfonate | 3% |
| Castor oil polyglycol ether (36 mol of EO) | 4% |
| Cyclohexanone | 30% |
| Xylene mixture | 50% |

Emulsions of any desired concentration can be prepared from this concentrate by diluting it with water.

| F7. Dusts | a) | b) |
| --- | --- | --- |
| Active substance No. 1.03 | 5% | 8% |
| Talc | 95% | — |
| Kaolin | — | 92% |

The ready-to-use dusts are obtained by mixing the active substance with the carrier and grinding the mixture on a suitable mill.

| F8. Extruder granules | |
| --- | --- |
| Active substance No. 1.03 | 10% |
| Na ligninsulfonate | 2% |
| Carboxymethylcellulose | 1% |
| Kaolin | 87% |

The active substance is mixed with the additives, and the mixture is ground and moistened with water. This mixture is extruded, granulated and then dried in a stream of air.

| F9. Coated granules | |
| --- | --- |
| Active substance No. 1.03 | 3% |
| Polyethylene glycol (MW 200) | 3% |
| Kaolin | 94% |

In a mixer, the finely ground active substance is applied uniformly to the kaolin which has been moistened with polyethylene glycol. In this manner, dust-free coated granules are obtained.

| F10. Suspension concentrate | |
| --- | --- |
| Active substance No. 1.03 | 40% |
| Ethylene glycol | 10% |
| Nonylphenol polyethylene glycol ether (15 mol of EO) | 6% |
| Na ligninsulfonate | 10% |
| Carboxymethylcellulose | 1% |
| 37% aqueous formaldehyde solution | 0.2% |
| Silicon oil in the form of a 75% aqueous emulsion | 0.8% |
| Water | 32% |

The finely ground active substance is intimately mixed with the additives. In this manner, a suspension concentrate is obtained from which suspensions of any desired concentration can be prepared by diluting it with water.

In the biological examples which follow, a good action means that the desired effect occurs to a degree of at least 50 to 60%.

EXAMPLE B1

Action against *Boophilus microplus*

Adult female ticks which have sucked themselves full are stuck onto a PVC plate and covered with a cotton-wool ball. For the treatment, 10 ml of an aqueous test solution containing 125 ppm of the active substance to be tested are poured over the test animals. The cotton-wool ball is then removed, and the ticks are incubated for 4 weeks to deposit eggs. The action against *Boophilus microplus* is demonstrated either on the female in terms of mortality or sterility, or on the eggs as an ovicidal action.

In this test, compounds of Table 1 have a good action against *Boophilus microplus*. In particular the compounds 1.01, 1.03 and 1.33 have an action of more than 80%.

EXAMPLE B2

Action against *Aedes aegypti*

50–100 *Aedes aegypti* larvae are introduced into 200 ml of an aqueous test solution containing 400 ppm of the active substance to be tested and a very small amount of feed. The test vessel is then sealed with a lid and incubated. The test is evaluated 14 days after it has been set up, for hatch % of the adults compared with untreated controls.

In this test, compounds according to Table 1 have a good action against *Aedes aegypti*. In particular the compounds 1.04, 1.22, 1.24 and 1.25 have an action of more than 80%.

EXAMPLE B3

Ovicidal action on *Cydia pomonella*

*Cydia pomonella* eggs which have been deposited on paper filters are briefly immersed in an acetonic-aqueous test solution containing 400 ppm of the active substance to be tested. After the test solution has dried on, the eggs are incubated in Petri dishes. After 6 days, the percentages of eggs where hatching is observed are evaluated by comparing them with untreated controls (% hatch reduction).

In this test, compounds according to Table 1 have a good action against *Cydia pomonella*. In particular the compounds 1.01, 1.04 and 1.05 have an action of more than 80%.

EXAMPLE B4

Ovicidal action on *Adoxophyes reticulana*

*Adoxophyes reticulana* eggs which have been deposited on paper filters are briefly immersed in an acetonic-aqueous test solution containing 400 ppm of the active substance to be tested. After the test solution has dried on, the eggs are incubated in Petri dishes. After 6 days, the percentages of eggs where hatching is observed are evaluated by comparing them with untreated controls (% hatch reduction).

In this test, compounds according to Table 1 have a good action against *Adoxophyes reticulana*. In particular the compounds 1.01, 1.05 and 1.12 have an action of more than 80%.

EXAMPLE B5

Ovicidal action against *Dermanyssus gallinae*

About 200 mites in various development stages and 2 to 3 ml of a solution containing 10 ppm of active substance are introduced into a glass vessel which is open at the top. The container is then sealed with a cotton-wool ball, shaken for 10 minutes until the mites are completely wetted, and then briefly turned over so that the remaining test solution can be absorbed by the cottonwool. After 3 days, the mortality of the mites is determined.

The compounds of Table 1 have a good action against *Dermanyssus gallinae*. In particular, the compounds 1.01, 1.05 and 1.22 have an action of more than 80%.

EXAMPLE B6

Action against *Aonidiella aurantii*

Potato tubers are infested with crawlers of *Aonidiella aurantii* (orange scale). After about 2 weeks, the potatoes are immersed in an aqueous emulsion spray liquor containing the active substance to be tested in a concentration of 400 ppm. After the treated potato tubers have dried, they are incubated in a plastic container. For evaluation after 10–12 weeks, the survival rate of the crawlers of the first consecutive generation of the treated scaly insect population is compared with that of untreated controls.

In this test, compounds according to Table 1 have a good action *Aonidiella aurantii*. In particular the compounds 1.01, 1.04 and 1.31 have an action of more than 80%.

EXAMPLE B7

Action against *Nilaparvata lugens*

Rice plants are treated with a spray liquor of an aqueous emulsion containing 400 ppm of the active substance. After the spray coating has dried on, the rice plants are infested with adult cicadas, which lay eggs. After this, the adults are removed and the plants are incubated. The tests are evaluated after 14 days. The percentage reduction of progeny (% action) is determined by comparing the number of hatched nymphae on the treated plants with those on the untreated plants.

The compounds of Table 1 have a good action against *Nilaparvata lugens* in this test. In particular, the compounds 1.01, 1.02, 1.04, 1.22, 1.24, 1.25 and 1.31 have an action of more than 80%.

EXAMPLE B8

Action against *Nephotettix cincticeps*

Rice plants are treated with a spray liquor of an aqueous emulsion containing 400 ppm of the active substance. After the spray coating has dried on, the rice plants are infested with adult cicadas, which lay eggs. After this, the adults are removed and the plants are incubated. The tests are evaluated after 14 days. The percentage reduction of progeny (% action) is determined by comparing the number of hatched nymphae on the treated plants compared with those on the untreated plants.

The compounds of Table 1 have a good action against *Nephotettix cincticeps* in this test. In particular, the compound 1.01 has an action of more than 80%.

EXAMPLE B9

Action against *Bemisia tabaci*

Dwarf beans are placed in gauze cages and infested with *Bemisia tabaci* adults (whitefly). After eggs have been laid, all adults are removed, and, 10 days later, the plants together with the nymphs living on them are treated with a spray liquor of an aqueous emulsion of the active substances to be tested (concentration 400 ppm). 14 days after the active substance has been applied, the population is evaluated for hatch % compared with untreated controls.

In this test, compounds according to Table 1 have a good action against *Bemisia tabaci*. In particular the compounds 1.01, 1.04, 1.22, 1.24 and 1.25 have an action of more than 80%.

I claim:

1. A compound of the formula Ia $$R_5\text{-phenyl(}R_6\text{)-O-phenyl-O-CH}(R_4)\text{-CH}(R_3)\text{-N}(COOR_1)(S(O)_n\text{-}R_2) \quad (Ia)$$

where $R_1$ is $C_1$-$C_4$alkyl or $C_3$-$C_4$alkenyl, $R_2$ is $C_1$-$C_4$alkyl or a radical of the formula phenyl($R_7$,$R_8$), -CH$_2$-phenyl($R_7$,$R_8$), -C(CH$_3$)$_2$-CN or -N(R$_9$)-COO-C$_1$-C$_4$alkyl, $R_3$ and $R_4$ independently of one another are hydrogen or methyl, $R_5$ is fluorine or chlorine, $R_6$ is fluorine when $R_5$ is fluorine or is hydrogen when $R_5$ is chlorine, $R_7$ and $R_8$ independently of one another are hydrogen, halogen, $C_1$-$C_4$alkyl, $C_1$-$C_4$alkoxy or nitro, $R_9$ is $C_1$-$C_4$alkyl and n is zero, one or two.

2. A compound according to claim 1, wherein $R_2$ is a radical of the formula phenyl($R_7$,$R_8$), -CH$_2$-phenyl($R_7$,$R_8$), or -C(CH$_3$)$_2$-CN and $R_5$ and $R_6$ are fluorine.

3. A compound according to claim 1, wherein $R_2$ is a radical of the formula phenyl($R_7$)

or -C(CH$_3$)-CN, $R_3$ and $R_4$ independently of one another are hydrogen or methyl, $R_5$ and $R_6$ are fluorine and $R_7$ is hydrogen, halogen, $C_1$-$C_4$alkyl, methoxy or nitro.

4. A compound according to claim 1, wherein $R_2$ is the radical phenyl($R_7$), $R_3$ and $R_4$ are hydrogen, $R_5$ and $R_6$ are fluorine, $R_7$ is hydrogen, chlorine, bromine or $C_1$-$C_4$alkyl, and n is zero or two.

5. A compound according to claim 1, wherein $R_1$ is $C_1$–$C_3$alkyl, $R_2$ is

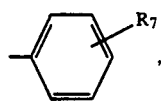

$R_3$ and $R_4$ are hydrogen, $R_7$ is hydrogen, chlorine, or methyl, and n is zero.

6. A compound according to claim 1, selected from the group consisting of

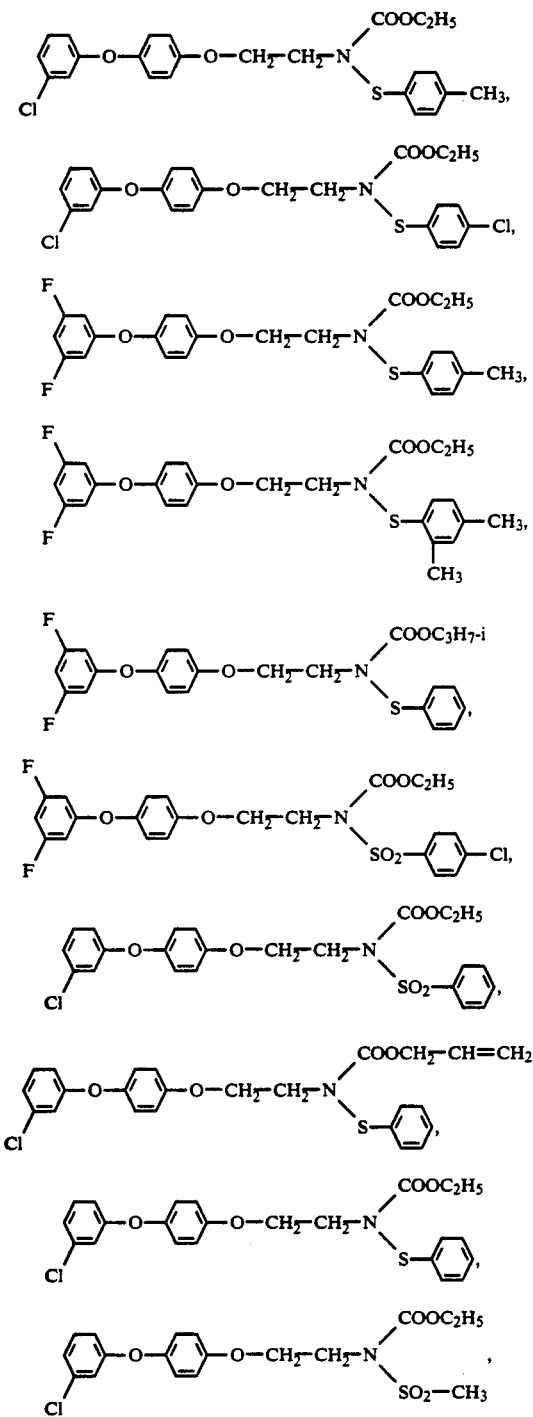

-continued

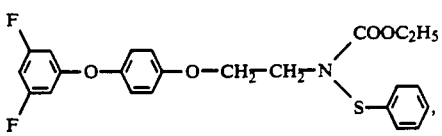

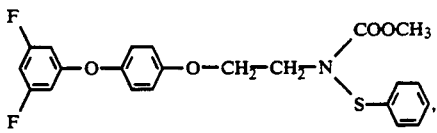

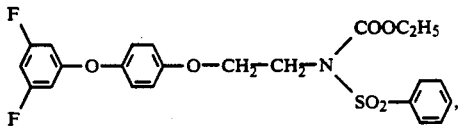

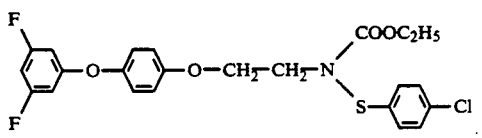

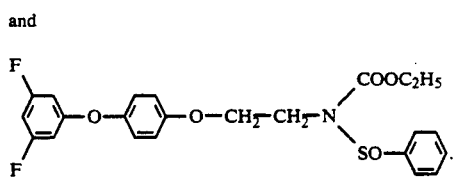

and

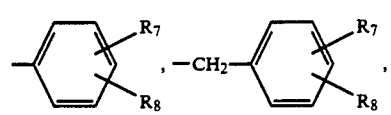

7. An insecticidal composition, containing, as the active component, at least an effective amount of a compound of the formula Ia
where $R_1$ is $C_1$–$C_4$alkyl or $C_3$–$C_4$alkenyl, $R_2$ is $C_1$–$C_4$alkyl or a radical of the formula

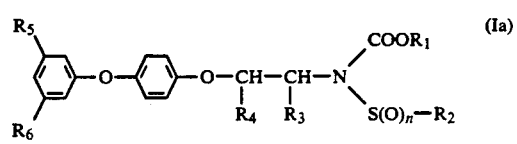

—$C(CH_3)_2$—CN or —$N(R_9)$—COO—$C_1$–$C_4$alkyl, $R_3$ and $R_4$ independently of one another are hydrogen or methyl, $R_5$ is fluorine or chlorine, $R_6$ is fluorine when $R_5$ is fluorine or is hydrogen when $R_5$ is chlorine, $R_7$ and $R_8$ independently of one another are hydrogen, halogen, $C_1$–$C_4$alkyl, $C_1$–$C_4$alkoxy or nitro, $R_9$ is $C_1$–$C_4$alkyl, and n is zero, one or two, and an agrochemically acceptable adjuvant.

8. A method of controlling insect pests on plants, animals and stored goods which comprises contacting any of the development stages of said pests or their locus with an insecticidally effective amount of a compound of the formula Ia $$R_5 \!\!-\!\!\bigcirc\!\!-\!\!O\!\!-\!\!\bigcirc\!\!-\!\!O\!\!-\!\!\underset{R_4}{CH}\!\!-\!\!\underset{R_3}{CH}\!\!-\!\!N\!\!\underset{S(O)_n-R_2}{\overset{COOR_1}{\diagup}} \quad \text{(Ia)}$$

where $R_1$ is $C_1$–$C_4$alkyl or $C_3$–$C_4$alkenyl, $R_2$ is $C_1$–$C_4$alkyl or a radical of the formula

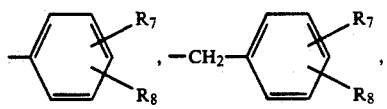

—C(CH$_3$)$_2$—CN or —N(R$_9$)—COO—C$_1$-C$_4$alkyl, R$_3$ and R$_4$ independently of one another are hydrogen or methyl, R$_5$ is fluorine or chlorine, R$_6$ is fluorine when R$_5$ is fluorine or is hydrogen when R$_5$ is chlorine, R$_7$ and R$_8$ independently of one another are hydrogen, halogen, C$_1$-C$_4$alkyl, C$_1$-C$_4$alkoxy or nitro, R$_9$ is C$_1$-C$_4$alkyl and n is zero, one or two.

9. A method according to claim 8 for destroying eggs of insects and ectoparasites which damage plants.

10. A method according to claim 8 for inhibiting the development of larvae of insects and ectoparasites which damage plants.